United States Patent [19]

Lindemans et al.

[11] Patent Number: 4,712,607
[45] Date of Patent: Dec. 15, 1987

[54] CRYOSYSTEM FOR BIOLOGICAL MATERIAL

[75] Inventors: Willem Lindemans; Lauri J. Aaltonen, both of Victoria, Australia

[73] Assignee: Freeze Control Pty. Ltd., Victoria, Australia

[21] Appl. No.: 796,328

[22] Filed: Nov. 8, 1985

[30] Foreign Application Priority Data

Nov. 9, 1984 [AU] Australia .................. PG8048

[51] Int. Cl.$^4$ .................. F25B 29/00; F25B 19/00
[52] U.S. Cl. .................. 165/30; 62/514 R
[58] Field of Search .................. 62/514 R, 64, 78, 381; 165/30, 80.1

[56] References Cited

U.S. PATENT DOCUMENTS

| | | |
|---|---|---|
| 3,827,251 | 8/1974 | Koski et al. .................. 62/514 R |
| 3,910,064 | 10/1975 | Gmelin et al. . |
| 4,001,944 | 1/1977 | Williams . |
| 4,117,881 | 10/1978 | Williams et al. . |
| 4,314,459 | 2/1982 | Rivoire .................. 165/30 |

FOREIGN PATENT DOCUMENTS

| | | |
|---|---|---|
| 0026691 | 4/1981 | European Pat. Off. . |
| 0101906 | 3/1984 | European Pat. Off. . |
| 0117037 | 8/1984 | European Pat. Off. . |
| 2657703 | 6/1978 | Fed. Rep. of Germany . |
| 2492210 | 4/1982 | France . |
| 146662 | 7/1931 | Switzerland . |

*Primary Examiner*—William E. Wayner
*Attorney, Agent, or Firm*—Merchant, Gould, Smith, Edell, Welter & Schmidt

[57] ABSTRACT

A cryo-cell assembly for biological material including a space for receiving the material, the space being at least partly enclosed by means suitable for conducting heat from the space to a heat sink and including heat generating means in heat conducting relationship with the space. Power is applied to the heat generating means according to a desired temperature cycle stored in memory. The power supply unit senses actual temperature in said space and compares this with the desired temperature. Power is supplied to the heat generating means whenever the actual temperature falls below the desired temperature.

15 Claims, 12 Drawing Figures

CRYOSYSTEM FOR BIOLOGICAL MATERIAL

The present invention relates to the field of cryopreservation. In particular the present invention relates to a system suitable for deep freezing and thawing living biological material.

Freezing and thawing of living biological materials between room temperature and say −190° (temperature of liquid nitrogen) requires considerable care and control if the living integrity of the material is to be maintained.

Samples of materials such as semen are typically frozen in straws (approximately 2 mm diameter and 130 mm length) so that each sperm cell is in close proximity to the walls of the straw through which cooling is performed.

To avoid or alleviate thermal shock at critical points in the freezing cycle changes in temperature must be carefully controlled.

One particular problem associated with freezing of tissue is the damaging formation of ice crystals. These may destroy cells membranes and even cell nuclei to the extent that recovery after thawing is not possible. To avoid such damage, water is sometimes removed from cells or buffered with antifreeze formulae.

Nevertheless precise control over the freezing cycle is required. Moreover a different freezing cycle is required for different kinds of tissues. For example, semen is often buffered so that its freezing point is reduced. Cooling rate is slowed during the crossing of 3 to −10° C. to ensure formation of only small elastic crystals.

Embryos are sometimes dehydrated at low temperatures and this requires constant temperature of −6° C. for approximately 30 minutes. Other tissues such as liver, spleen, glandular material, blood fractions and botanical "gene bank" material all have specific freezing requirements.

Apparatus for performing such freezing cycles is known. However currently existing apparatus is both expensive and bulky. Existing apparatus of this type therefore is generally location based, and is not readily adapted to portable or field use. Moreover, the demand for such apparatus has expanded greatly. In particular there is a need for compact apparatus which may be portable so that a collector can freeze specimens in the 'field'.

A further disadvantage of certain prior art machines concerns their reliability. Apparatus which utilizes moving parts such as mechanical valves for injecting liquid nitrogen ($LN_2$) etc. may be prone to breakdown. Moreover such apparatus consumes relatively large quantities of $LN_2$, e.g. 10–15 liters per cycle.

It is an object of the present invention to alleviate the disadvantages of the prior art. It is a further object of the present invention to provide apparatus for freezing and/or thawing biological material which may be constructed in compact dimensions, thus making it suitable for field work and other applications where portability is desirable. It is a still further object of the present invention to provide such apparatus at significantly lower cost relative to existing apparatus. At the very least the apparatus of the present invention should provide the public with a choice.

The apparatus of the present invention is based on the thermal bridge principle, i.e. the apparatus operates by locating a heat source and a heat sink in heat conducting relationship with the biological material to be processed.

The apparatus of the present invention includes a cryo-cell assembly. The cryo-cell assembly may include a space for receiving biological material to be processed. The cryo-cell assembly preferably includes a source of heat positioned in heat conducting relationship with said space.

The cryo-cell assembly of the present invention may be provided in any convenient form. The cryo-cell assembly preferably is adapted to generate substantially concentric isotherms within the space for receiving biological material.

The cryo-cell assembly preferably comprises a plurality of nested members. The assembly may include an innermost or core member, a thermally insulating layer and an outer member surrounding the insulating layer. The innermost or core member may be arranged in heat conducting relationship with the space for receiving biological material. The core member preferably comprises a tubular member. The core member may include one or more slots formed, about the perimeter of the core member. The slots preferably extend longitudinally along the core member. The slots may be formed in the inner or outer wall surface of the core member.

The inner core member may be formed of any suitable material. The inner core member may be formed of a material having good thermal conductivity such as copper, aluminium or silver. Good grade aluminium (i.e. one having high purity) is preferable. The inner core member may be formed in any suitable manner e.g. by extrusion or machining. The slots may be formed with the core member or they may be machined therein after forming.

Preferably the slots are substantially evenly spaced around the perimeter of the core member. The or each slot may be adapted to accept 2 mm diameter specimen straw. In one form the slots may be milled on the internal wall of the core member. The slots may be milled to a depth and width of approximately 3 mm. One slot may be formed slightly larger than the others for accepting a temperature sensor.

Where the slots are formed on an external wall of the core member, the assembly may include an intermediate member surrounding the core member. The intermediate member preferably comprises a tubular member. The intermediate member may be arranged in heat conducting relationship with the core member.

The intermediate member preferably is slidably fitted over the inner core member. The inner core member may be slidable relative to the intermediate member to facilitate removal and placement of samples. A suitable base member may be attached to one (the lower) end of the inner core member or to the intermediate member. The base member may be adapted to support specimen straws and/or to prevent liquids or other materials penetrating into the insulating layer of the assembly. The supporting base preferably comprises a flat plate. The plate may be approximately circular and of a diameter similar to the internal diameter of the intermediate member.

A suitable handle may be attached to the core member to facilitate its removal from the assembly. The handle may comprise e.g. a wire frame bent to an inverted U shape and held to the core member. The handle and supporting base member preferably comprise stainless steel.

Where slots are formed on the internal wall of the core member, the intermediate member may be dispensed with. Specimen straws may be placed into and removed from the assembly without moving the inner core member. A suitable support frame may be provided for supporting specimen straws. The support frame may be adapted to slide into the core member. The support frame may include a handle to facilitate manipulation of specimen straws.

In one form the support frame may comprise an elongate member having a plurality of support elements at one end thereof. The support elements may extend radially from the elongate member and substantially perpendicular to the elongate member. Each support element may be adapted to engage and support the lower end of a specimen straw.

The cryo-cell assembly includes heat generating means. The heat generating means may be adapted to surround the intermediate member and/or the inner core member. The heat generating means preferably includes a heater element adapted to surround the intermediate member and/or the inner core member.

In one form the heat generating means comprises a heater element wound around the external wall of the intermediate member. Where specimen receiving slots are formed on the internal wall of the core member the heater element may be wound directly onto the external surface of the core member. The heater element preferably comprises resistance wire such as nichrome wire. The resistance wire element may be wound around the intermediate member with uniform spacing between the windings. The heater element preferably comprises a pair of windings having parallel windings evenly spaced with current passing in opposite directions to minimize magnetic field effects in the vicinity of the heater element and specimen.

The intermediate member may include a pair of helical grooves cut into its external wall surface for retaining the heater element. The helical grooves may be substantially uniformly distributed over the length of the intermediate member. In one form the helical grooves may comprise a pair of parallel threads having a pitch of 2 per cm each and a depth of 0.5 mm. The resistance wire may be wound into one of the grooves and returned along the other groove to minimize the previously noted magnetic field effects. In one form the resistance of the heating element may be approximately 30 ohms.

The thermally insulating layer may be adapted to surround the heater element. The insulating layer may be provided in any suitable manner. The insulating layer may comprise wood, felt, foam or other suitable material. The insulating layer may be formed in any suitable form. The insulating layer may comprise a sleeve of selected grade insulating material. The grade of insulating material may be selected to provide the optimum flow rate of heat between the core member and outer member. In one form the insulating material may be selected to have a heat conduction of 1 mW/cm° C. The insulating layer may be wound evenly around the intermediate member or be pre-formed and fitted over the intermediate member. Alternatively the insulating layer may be injection molded into the cavity between the intermediate member and the outer member of the cryo-cell assembly.

The intermediate member and insulating layer may be firmly fitted into the outer member. After fitment, the gap formed between the top edges of the intermediate and outer members (annular where the assembly is cylindrical) preferably is sealed to minimize penetration of moisture into the insulating layer. A pair of connecting leads for carrying current to the heater windings may be passed through the seal.

The outer member which may comprise the housing of the cryo-cell assembly preferably comprises a tubular member surrounding the insulating layer. The outer member preferably includes a base. The base may comprise a plate or a cap member fitted at one end of the outer member. The plate preferably is welded or soldered across the opening with suitable solder material. The cap preferably is retained in the end of the outer member by means of an interference fit, e.g. the cap may be pressure fitted or crimped onto the end of the outer member.

The outer member or housing preferably comprises a material having good thermal conductivity. Copper or high purity aluminium is preferable for this purpose. The outer member or housing may be formed in any convenient manner e.g. by extrusion or machining.

The nested members of the cryo-cell assembly may comprise substantially cylindrical tubular members. The tubular members preferably are concentric. The arrangement preferably is such that heat flow is uniformly radial and layers are cylindrical isotherms. In particular all specimen and the temperature sensors may have the same temperature both around the core member and along it.

The cryo-cell assembly of the present invention may be formed with any suitable dimensions. Preferably the cryo-cell assembly of the present invention is of the order of several centimeters in diameter (4–5 cm) and of the order of 15 cm in height.

A closure may be provided for closing the top of the cryo-cell assembly. The closure may be opened to permit insertion of monitoring devices and/or application of additional coolant to the core for fast cooling. The closure cap may be formed of any suitable material, preferably stainless steel. The closure cap may include an insulated handle.

The cryo-cell assembly may be provided with a suitable handle. The handle preferably is insulated to facilitate handling of the assembly.

The cryo-cell assembly of the present invention is adapted to be placed into a flask or cup filled with $LN_2$ which acts as a heat sink. The freezing rate may be controlled by warming the heating element.

The cryo-system of the present invention may include a control unit for controlling the freezing cycle. The control unit preferably is programmable. The control unit may be adapted to adjust the level of current supplied to the heater windings.

The control unit preferably incorporates feedback means for comparing the actual temperature at the core of the cryo-cell assembly with the desired temperature.

The control unit includes temperature sensing means. The temperature sensing means includes a temperature sensing element. The temperature sensing element may be provided in any suitable manner. Preferably the temperature sensing element comprises a resistance element such as platinum wire or a string of diodes connected in series. The sensing element may be inserted into a straw of the kind used for storing specimens. Where diodes are used the diodes preferably are spaced substantially uniformly along the length of the straw. The straw may be placed in a slot of the core member in the manner of the specimen.

A relatively low but constant biasing current, say 2.5 mA may be passed through the resistance element. A relatively lower biasing current, say 1 uA, may be passed through the diodes. It has been found that the diodes have good temperature sensitivity and fairly linear response over the operating temperature range at relatively low current levels.

A constant current source may be used to supply biasing current to the temperature sensing element. The constant current source may be generated by any suitable means. In one form the current source may include a resistor. The resistor preferably exhibits a low temperature coefficient. Alternatively the constant current source may be generated by means of a suitably biased field effect transistor. The temperature sensing means may include amplifying means for amplifying the voltage generated across the temperature sensing element. The amplifying means preferably comprises an operational amplifier with FETs at its input.

A temperature display means may be operatively connectable to the temperature sensing means. The display means may include scaling means. The scaling means may be provided in any suitable manner. The scaling means preferably comprises an operational amplifier. The gain and off-set of the operational amplifier may be adjustable by means of adjustable elements such as potentiometers.

The temperature display means preferably includes a display element such as a voltmeter. A digital voltmeter is preferred for this purpose.

The control unit may be adapted to generate a signal representing the desired temperature. The desired temperature generally will be a time dependent variable. It is desirable to vary the temperature cycle of the cryocell assembly according to the nature of the biological material being frozen.

The control unit preferably is arranged such that the temperature cycle may be readily changed or reprogrammed. The control unit may include digital processing means for storing one or more temperature cycle programs.

The control unit preferably includes clock means for providing timing pulses to the processing means. The clock means may be provided in any suitable manner. The clock means preferably includes an oscillator. In one form the oscillator may comprise an inverting amplifier and associated feedback circuit. The feedback circuit may include an RC network or a crystal element. The crystal element may be adapted to oscillate at a frequency of 3.58 MHz. Preferably the inverting amplifier comprises a Schmitt triggered CMOS NAND gate.

The clock means may include frequency dividing means. The dividing means may comprises a divide counter by $2^N$ counter. The dividing means may comprise a circuit type CD 4020 14 stage ripple counter. In one form the dividing means may be adapted to divide the clock frequency by a factor of $2^{14}$. In another form the dividing means may comprise one or more binary counters.

The clock means preferably includes means for adjusting its frequency. The frequency adjusting means may be provided before or after the frequency dividing means. The oscillator may include a turn over switch for "fast" or "slow" clock frequency. In one form the oscillator frequencies may be scaled to provide frequencies of 3.2 KHz and 500 Hz respectively. In another form the oscillator frequencies may be scaled to provide frequencies of 1.7 Hz and 0.12 Hz respectively.

The processing means may include an address generator for generating a binary address. In one form the address generator maybe adapted to provide an 8-bit address. The address generator preferably comprises a counter having parallel outputs. A pair of 4-bit counters may be used in series for this purpose. In one form the address generator may comprise a pair of circuit type MM74C193 up/down binary counters. In another form the address generator may comprise a circuit type 4040 twelve stage binary counter. The processing means may include an address display means for displaying the address. The address display means may comprise a row of LEDs. The processing means may additionally or alternatively comprise means for displaying elapsed program time. Means for displaying elapsed program time may include a digital to analogue converter and a voltage display means such as a digital voltmeter.

The processing means preferably includes means for selecting a particular program. The program selector may be provided in any suitable manner. In one form the means for selecting a program may comprise a binary switch, e.g. a 3-bit binary switch may be used for selecting any one of up to eight programs. In one form the binary switch comprises a thumbwheel switch.

The processing means may comprise a microprocessor or microcomputer. The processing means may alternatively comprise a digital computer remote from the control unit of the present invention. The remote computer may be connected to the control unit via a suitable interface (serial or parallel). The interface may include an RS232 socket or a suitable parallel connection. The control unit preferably includes storage means. The storage means may include a ROM (Read Only Memory).

Preferably the ROM comprises a programmable ROM. The processing means may comprise an EPROM (Erasable Programmable ROM). In one form the processing means comprises a circuit type MM 27C16 EPROM.

Preferably the EPROM is adapted to receive an 11-bit address. The EPROM may be adapted to receive an 8-bit address signal from the address generator and a further 3-bit address signal from the program selector.

The EPROM may be programmed in accordance with known techniques. The EPROM may be adapted to store one or more temperature cycles or programs. Any one cycle may be selected to suit a particular type of biological material or preparation or to choose between freezing and thawing. In one form up to eight different temperatures cycles or programs may be stored in the EPROM.

The or each program maybe adapted to increase or decrease temperatures at a specified rate or to hold a temperature for a specified period of time. Any number of such variations may occur within a given program or cycle. In one form the control unit may be adapted to control temperatures between 20° C. and −44° C. in say 0.25° C. steps. In another form the control unit may be adapted to control a larger temperature range e.g. between 40° C. and −190° C. with a higher or lower resolution per step.

The control unit may include a digital to analogue converter (DAC). The DAC may be adapted to convert temperature signals provided in digital form by the processing means to corresponding analogue temperature signals representing desired temperature.

The DAC may be provided in any suitable manner. The DAC preferably comprises a single integrated device. In one form the DAC may comprise an 8-bit current mode device such as a circuit type DAC 0800. In another form the DAC may comprise a higher resolution 16 bit device. Alternatively the function of the DAC may be provided via an external computer system.

The control unit may include means for comparing the sensed temperature with the desired temperature stored in the program. The comparison means may be provided in any suitable manner. In one form the comparison means may comprise a current summing junction. The summing junction may be provided via the input of an operational amplifier.

The output of the temperature sensing means may be connected to one input of the comparison means via suitable buffer means, such as an operational amplifier. The (analogue) output of the DAC may be connected to the second input of the comparison means. The comparison means may be adapted to provide an output signal which is proportional to the difference between the measured and the desired temperature. The output of the comparison means may be adapted for controlling a heater control means. The heater control means may comprise a switching means for switching power to the heater of the cryo-cell assembly.

The heater control means may be provided in any suitable manner. Preferably the heater control means includes a solid state switching device. The switching device may comprise one or more power transistors or a silicon controlled rectifier (SCR). In one form the switching device comprises a power darlington.

The heater control means may be adapted to provide continuous or switched power to the heater of the cryo-cell assembly. To minimize heat dissipation in the switching device it is preferable to switch power to the heater.

In one form, the heater control means may be adapted to provide pulse width modulation of the switched power to the heater. Pulse width modulation may be provided in any suitable manner. In one form the pulse width modulator may include a ramp generator and a comparator.

The ramp generator may be provided in any suitable manner. The ramp generator may include an integrating circuit. The integrating circuit may be adapted to receive a square wave input from an oscillator. This oscillator signal may be provided by the clock means at a frequency of say 3.2 KHz or 500 Hz.

The comparator of the pulse width modulator may be adapted to compare the output of the ramp generator with the reference output of the temperature comparison means.

Whenever the reference voltage exceeds the highest ramp voltage, the comparator of the pulse width modulator may be adapted to turn off the solid state switch and hence turn off the power to the heater.

Whenever the reference voltage falls below the lowest ramp voltage, the comparator of the pulse width modulator may be adapted to turn on the solid state switch and hence supply full power to the heater.

When the reference voltage falls between the limits of the highest and lowest ramp voltages, the comparator of the pulse width modulator may be adapted to switch on the solid state switch for the duration of time that the reference voltage remains below the instantaneous ramp voltage.

The above arrangement may thus be adapted to trigger the solid state switch with a pulse width modulated signal. The duration or width of the or each pulse may be determined by the instantaneous value of the reference voltage of the temperature comparison means. The heater control means preferably is arranged such that the proportion of time that the solid state switch supplies power to the heater increases as the sensed temperature decreases below the desired or programmed temperature.

The power supply to the control unit may be provided in any suitable manner. The control unit may be mains powered or it maybe powered from an auxiliary power supply (AC or DC) e.g. a car battery.

Figure 1:
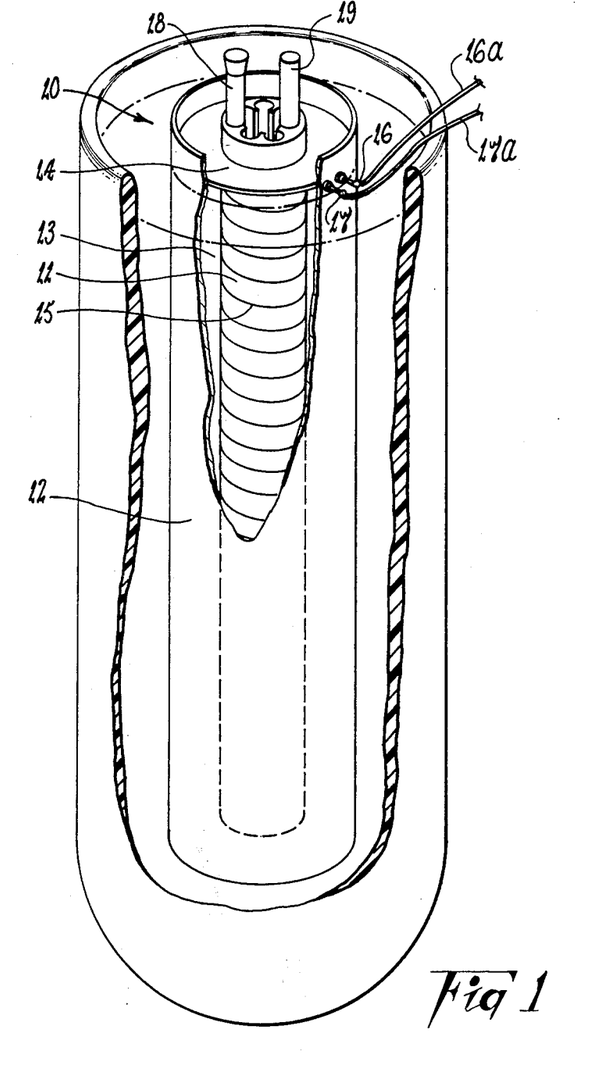
FIG. 1 shows a cut away view of a cryo-cell assembly according to a preferred embodiment of the present invention.

Preferred embodiments of the present invention will now be described with reference to the accompanying drawings wherein:

FIG. 1 shows a cryo-cell assembly shown generally at standing in a flask of $LN_2$. The cryo-cell assembly comprises an inner core member 11 and an outer member 12.

Inner core member 11 comprises a substantially cylindrical member formed of high grade aluminium and will be further described with reference to FIGS. 2–6. Outer member 12 comprises a tubular member having a substantially annular cross-section formed of copper.

The outer and inner core members are separated by a thermally insulating material 13. The insulating material 13 may comprise a selected insulating grade foam. The insulating material 13 may be injected into the substantially annular cavity between the outer and inner members.

Outer member 12 includes a cap or base also formed of copper (not shown) fitted at its lower end. A sealing member 14 adapted to minimize contamination of the insulating material 13 is applied to the annular opening at the top of the cell assembly.

Core member 11 includes a heater coil 15 wound around its outer wall. Heater coil 15 comprises a 7 meter strand of plastics coated 23 gauge ni-chrome wire (4.3 ohms/m) with total resistance of 30.1 ohms seated in a helical groove formed in the wall of the core member.

The two ends of the heater coil 15 are passed through outer member 12 to terminals 16, 17 respectively for connection to a suitable supply of electric currents via leads 16a, 17a.

The cryo-cell assembly is shown with straws 18, 19 inserted into the core member 11. One of the straws 18, 19 may hold a temperature sensor such as a diode string.

It will be appreciated that the above construction generates substantially cylindrical concentric isotherms within the core member. Each straw (including the temperature sensor) preferably is located in a common isotherm so that each straw is subjected to the same or substantially similar temperature environment.

The cryo-cell is placed in a Dewar flask of liquid nitrogen ($LN_2$).

FIGS. 2-6 show alternative embodiments for the inner core member 11. The core member of FIG. 2 comprises a thick walled tubular member 20 formed of high thermally conductive aluminium. Evenly spaced slots 21 are milled longitudinally or extruded on the internal wall of the core member. Each slot may be silled to a depth and width of 3 mm. The slots will accept 2 mm specimen straws. One slot may be slightly larger than the rest to accept the temperature sensing tube or straw.

Figure 2:
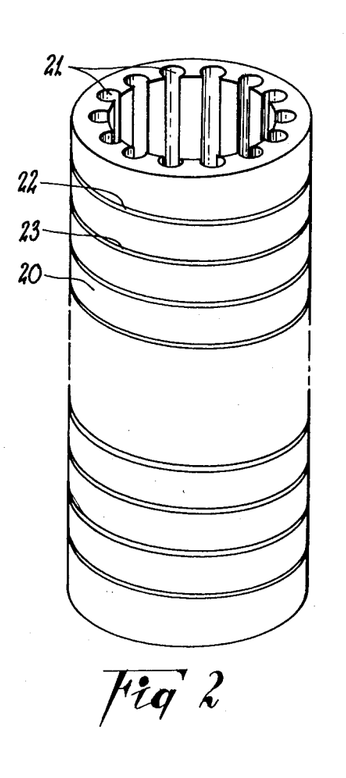
FIG. 2 shows one form of core member suitable for use with the cryo-cell of the present invention.

The base of the core member may be capped to prevent liquids and other contaminants penetrating into the insulating layer.

A support frame made of a suitable material such as stainless steel or plastics may be inserted into the core member for supporting the straws. The support frame may comprise an elongate member with a handle at one end and a plurality of radially extending supports or fingers at the opposite end, for supporting the straws.

A pair of parallel helical grooves 22, 23 are formed in the external surface of the core member for receiving the heater coils. The grooves preferably have a depth of 0.5 mm and a pitch of 2 per cm each.

Figure 3:
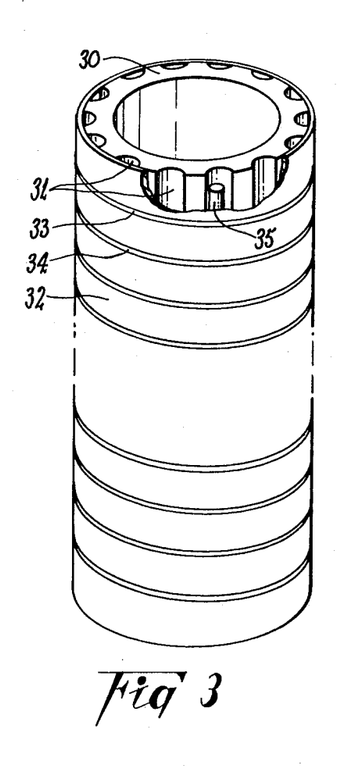
FIGS. 3 to 6 show alternative forms of core member suitable for use with the cryo-cell of the present invention.

The core member of FIG. 3 comprises a thickwalled tubular member 30 formed of high thermally conductive aluminium. Evenly spaced slots 31 for specimen straws are milled on the outside wall or extruded to a width and depth of 3 mm. One slot is slightly larger to accept the temperature sensor. An aluminium sleeve member 32 is fitted over the core member 30 such that the core member 30 is able to move freely up and down with respect to the sleeve member 32. The core member 30 includes a stainless steel base plate (not shown) for supporting specimen straws. A wire frame handle (not shown) may be attached to the core member to facilitate extraction of the core and straws.

A pair of parallel helical grooves 33, 34 are formed in the external surface of the sleeve member for receiving the heater coils. Sleeve member 32 is capped at the bottom to minimize penetration of liquid into the insulating layer.

A 3 mm aluminium tube 35 is attached along the inside wall of the sleeve member 32 so that it meshes with one of the slots 31 in core member 30. This tube may be used to house the temperature sensor.

Figure 4:
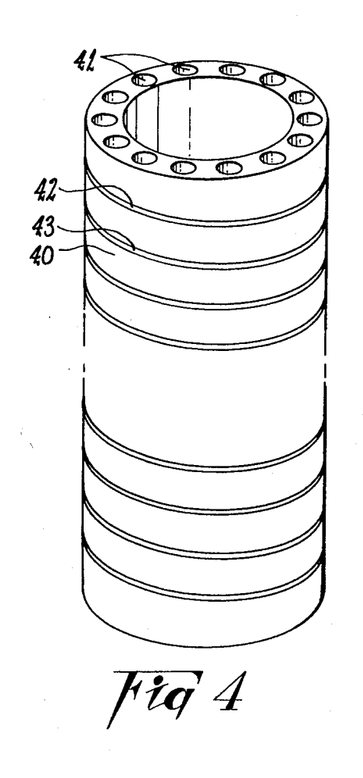

A further form of core member is shown in FIG. 4. The core member of FIG. 4 comprises a thickwalled tubular member 40 formed of high thermally conductive aluminium. Evenly spaced substantially parallel holes 41 are drilled longitudinally around the perimeter of the core member 40 for receiving specimen straws. A pair of parallel helical grooves 42, 43 are formed in the external surface of the core member for receiving heater coils.

Figure 5:
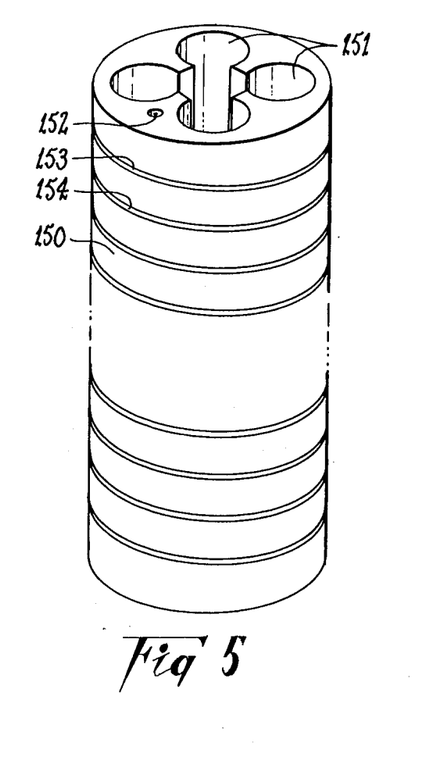

The Core member of FIG. 5 comprises a member 150 formed of high thermally conductive aluminium. Evenly spaced substantially parallel holes 151 are drilled longitudinally in the member for receiving ampules carrying specimens. A smaller hole 152 is formed longitudinally in the member 150 for housing the temperature sensor. A pair of parallel helical grooves 153, 154 are formed in the external surface of the core member for receiving heater coils.

Figure 6:
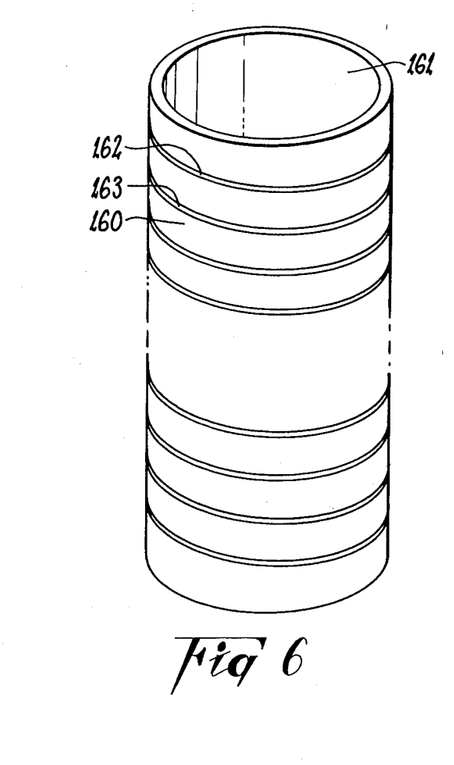

The core member of FIG. 6 comprises a tubular member 160 formed of high thermally conductive aluminium. A single bore 161 is formed longitudinally in the member for receiving larger specimens. A pair of parallel helical grooves 162, 163 are formed in the external surface of the core member for receiving heater coils.

Figure 7:
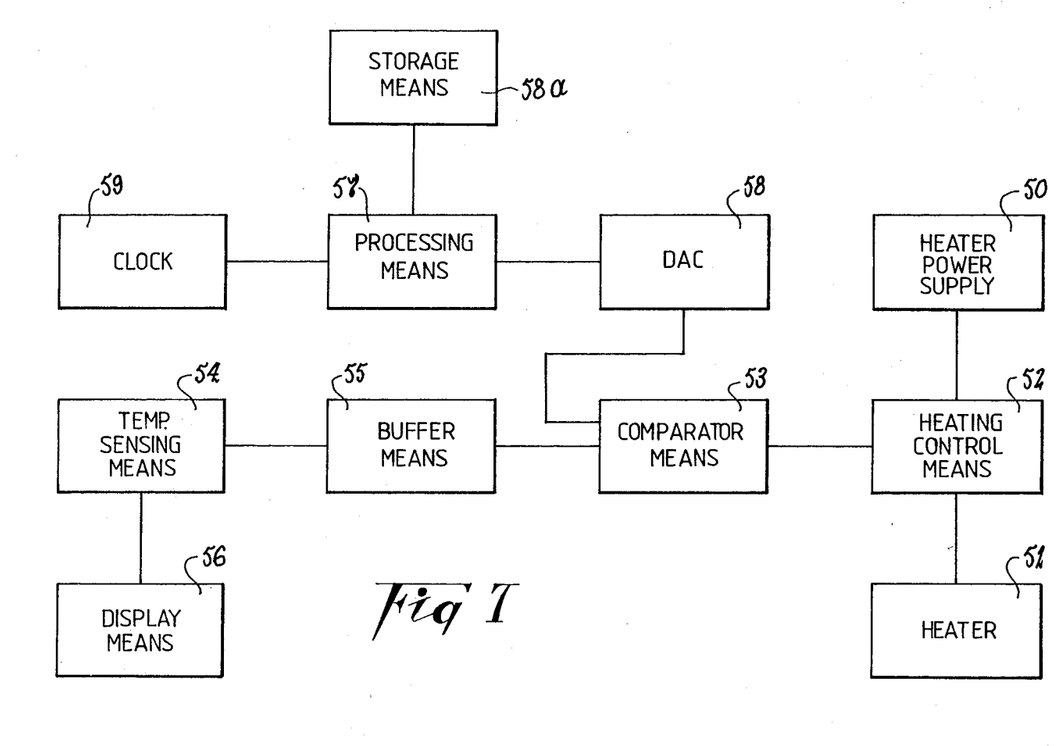
FIG. 7 shows functional or block diagram of a control unit according to a preferred embodiment of the present invention.

Referring to FIG. 7, the control unit supplying electrical power 50 to the heater 51 includes heating control means 52 triggered by a comparator means 53.

Comparator means 53 receives a signal representing 'actual' temperature from temperature sensing means 54 via buffer means 55. The control unit includes display means 56 for displaying the sensed or actual temperature.

Comparator means 53 also receives a signal representing desired temperature from processing means 57 via Digital to Analogue convertor (DAC) 58. Processing means 57 receives information regarding 'desired' temperature from one or more programmes stored in storage means 58a. Clock 59 provides clock pulses to processing means 57.

Figure 8:
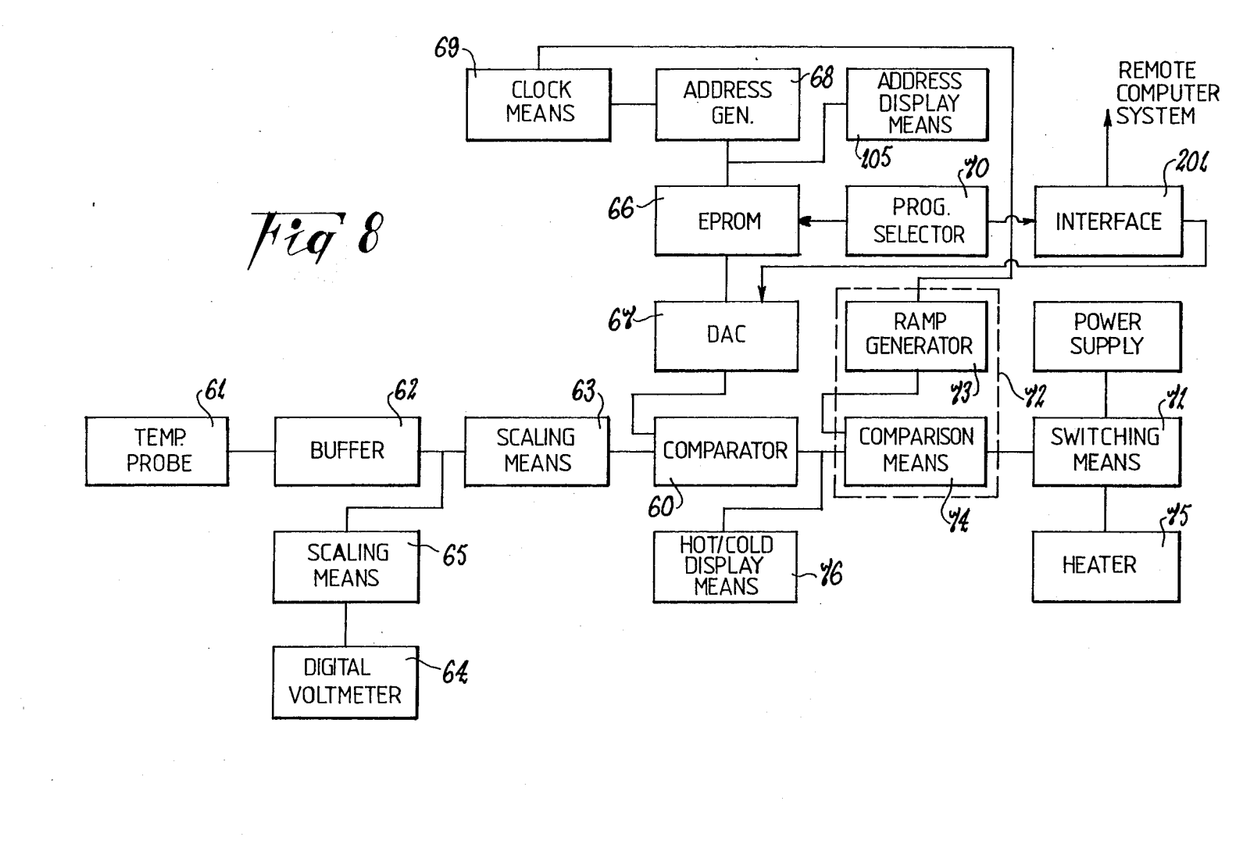
FIG. 8 shows a further block diagram of a control unit according to a preferred embodiment of the present invention.

FIG. 8 shows in greater detail a preferred form of control unit according to the present invention. The control unit shown in FIG. 8 includes a temperature signal comparator 60 receiving an 'actual' temperature signal from temperature probe 61 via buffer 62 and scaling means 63.

Temperature display is provided by a digital voltmeter 64 connected to the output of buffer 62 via scaling means 65.

Comparator 60 receives a 'desired' temperature signal from EPROM 66 via DAC 67. EPROM 66 is driven by an address generator 68 and clock means 69. Address display means 105 is also driven by address generator 68. The control unit includes program selector 70 for selecting one of the temperature programs or cycles stored in EPROM 66.

The output of temperature comparator 60 is used to control switching means 71 via pulse width modulator circuit 72. Pulse width modulator circuit 72 comprises ramp generator 73 and comparator 74. The output of comparator 74 drives switching means 71 for controlling supply of power to heater 75.

Hot/cold display means 76 is connected to the output of temperature comparator 60 for displaying when the 'actual' temperature is above (hot) or below (cold) the 'desired' temperature in a given program cycle.

The control unit of the present invention may be connected to a remote computer system via a suitable interface 201. Interface 201 may include a serial socket connection such an an RS232.

Figure 9:
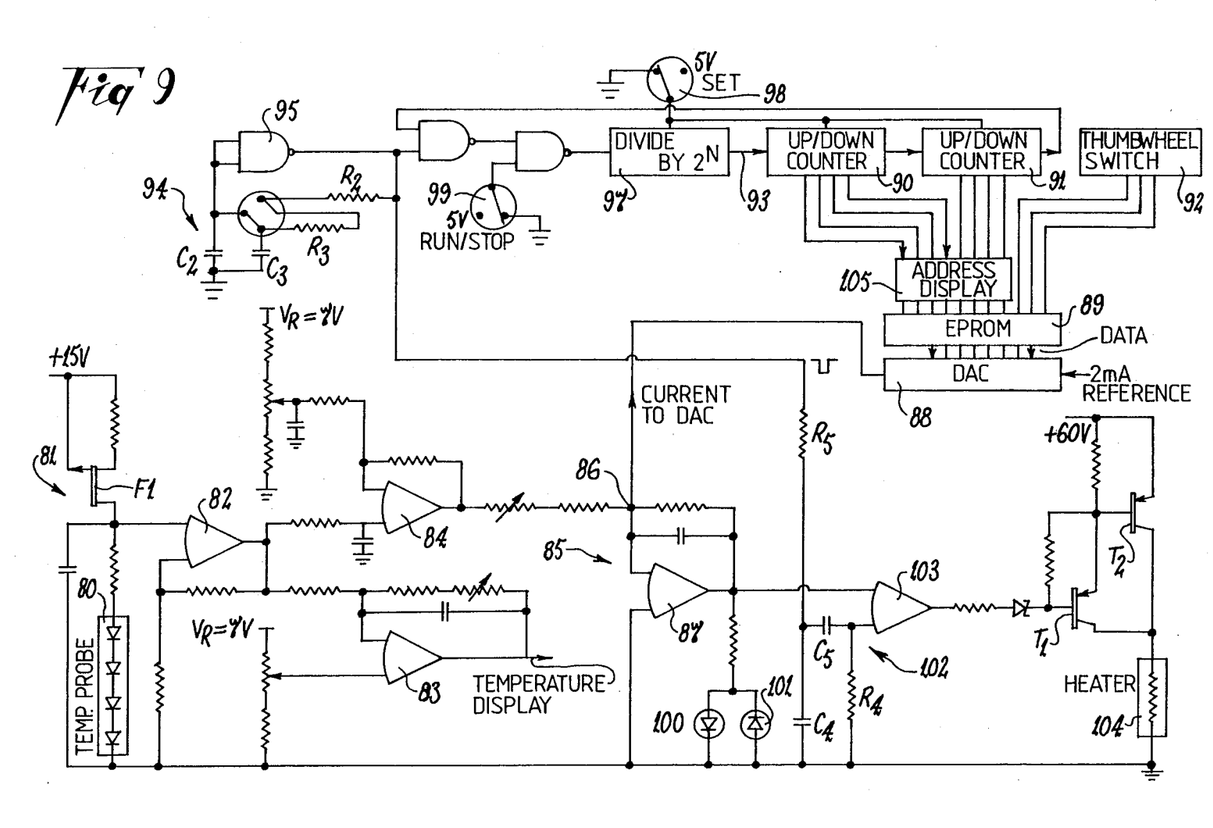
FIG. 9 shows a schematic circuit diagram of a control unit according to one preferred embodiment of the present invention.

Referring to FIG. 9, there is shown a schematic circuit diagram of one form of control unit according to the present invention.

The control unit includes a temperature probe comprising a string of diodes 80. Each diode may comprise a small glass encapsulated silicon device having good temperature sensitivity such as a circuit type AB203. The diodes may be batch selected for this purpose.

The string of diodes may be inserted into a specimen straw and placed into the core member of the cryo-cell assembly previously described.

A suitable biasing current e.g. 1 uA may be applied to the string of diodes 80 via a constant current source shown generally at 81. Current source 81 comprises a suitably biased field effect transistor F1 chosen for its pinch off temperature stability, such as a circuit type PN 4360.

It will be appreciated that as the junction temperature of each diode changes so also does the energy of charge carriers in the diode which leads to a change in the forward bias voltage across each diode junction. By measuring the resulting voltage across the diodes 80, a measure of the junction temperature may be obtained.

The voltage across the diodes 80 is applied to the input of buffer amplifier 82 which comprises a type with FET inputs. The output of buffer 82 is applied via scaling amplifier 83 to a temperature display device such as a digital voltmeter.

The output of buffer 82 is further applied via scaling amplifier 84 to a comparison circuit shown generally at 85. Comparison circuit 85 includes a current summing junction 86 at the inverting input of amplifier 87.

The summing junction receives positive current from the scaling amplifier 84 and negative current input from digital to analogue convertor (DAC) 88. When the two currents are equal and opposite the output of amplifier 87 is zero. DAC 88 comprises a current mode device such as a circuit type DAC 0800 driven by a 2 mA reference current.

DAC 88 is fed with digital data stored in EPROM 89. EPROM 89 is adapted to store one or more temperature cycles or programs for freezing and/or thawing given biological materials. EPROM 89 may comprise a device type MM27C16.

EPROM 89 is driven by an address generator comprising counters 90, 91. Each counter 90, 91 comprises a 4-bit up down counter. Counters 90, 91 are connected in series to provide in effect an 8-bit address generator. Each counter 90, 91 may comprise a device type MM74C193. The 8 address lines are also connected to address display 105 which includes a set of LED indicators (not shown). The LEDs display the current position in the program.

A 3-bit thumbwheel switch 92 also is connected to EPROM 89. Thumbwheel switch 92 may be used for selecting a given temperature program or cycle stored in EPROM 89.

Address generator counters 90, 91 are fed with clock pulses along line 93. Clock pulses are provided by a clock generator including an oscillator shown generally at 94. Oscillator 94 includes NAND gate 95 and a feedback network comprising resistors $R_2$, $R_3$ and capacitors $C_2$, $C_3$. The NAND gate may comprise a CMOS Schmitt trigger device type CD 4093. Oscillator 94 may be set to any convenient frequency. Preferably the frequency is adjustable. A frequency switch 96 may be provided for this purpose. In one form the oscillator frequency may be set at 3.2 KHz. In another form the frequency may be 500 Hz. Frequency switch 96 may be adapted in one form to switch between two frequencies, say 500 Hz and 3.2 KHz.

The clock generator includes means for dividing the frequency of oscillator 94. The frequency dividing means includes divide by $2^N$ divider 97. Divider 97 may be set to divide by $2^{14}$. Divider 97 may comprise a device type CD 4020.

Reset switch 98 is provided for resetting counters 90, 91 and divider 97. Clock run/stop switch 99 is provided for stopping the clock pulses to the divider 97. Switch 99 may be used to start a program sequence or to pause in the sequence at any time.

It will be appreciated that the output of temperature comparison circuit 85 (amplifier, 87) will swing high (positive) or low (negative) depending on whether the 'actual' temperature is higher or lower than the 'desired' temperature. A pair of LEDs 100, 101 may be connected to the output of amplifier 87 to display when the 'actual' temperature is lower (too cold) or higher (too hot) than the 'desired' temperature.

The output of amplifier 87 also drives a heater control circuit. The heater control circuit includes a pulse width modulator shown generally at 102 and a solid state switch including darlington transistor pair $T_1$, $T_2$. Darlington pair $T_1$, $T_2$ may comprise device types TIP 32C, TIP 36C respectively.

Pulse width modulator 102 includes comparator 103 and an integrating circuit comprising resistors $R_4$, $R_5$ and capacitors $C_4$, $C_5$. The integrating circuit receives substantially a square signal from oscillator 94 and converts these to a rising and falling ramp signal at the inverting input of comparator 103.

Comparator 103 compares the reference voltage at its non inverting input representing high/low temperature with instantaneous ramp voltage at its inverting input. The output of comparator 103 is high when the reference voltage is higher than the instantaneous ramp voltage and low when the reference voltage is lower than the instantaneous ramp voltage.

Comparator 103 is adapted to switch the darlington pair $T_1$, $T_2$ into conduction when its output is low and hence supply power to heater 104. When the output of comparator 103 is high, the darlington pair is turned off and no power flows to heater 104.

Each amplifier 82, 83, 84 and 87 may comprise a device type LF412. Comparator 103 may comprise a device type LF411. NAND gates used in the circuit may comprise a device type CD4093.

Figure 10:
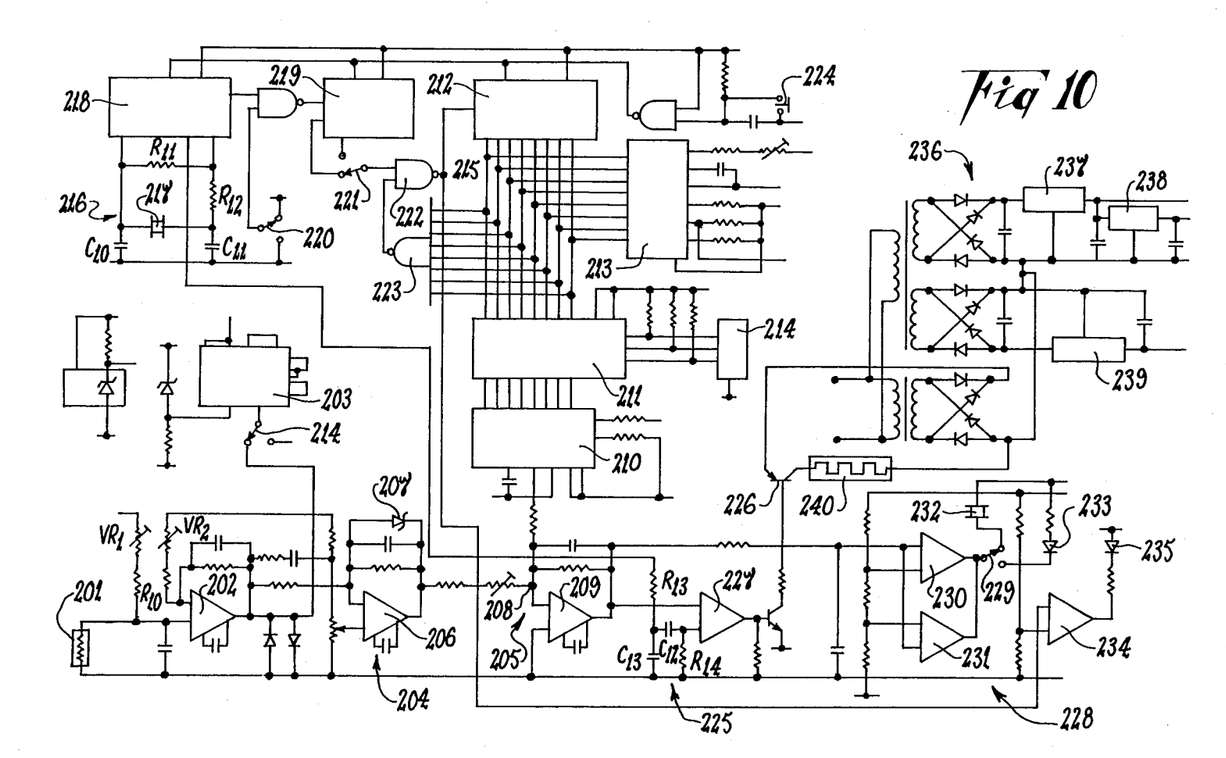
FIG. 10 shows a schematic circuit diagram of a control unit according to another preferred embodiment of the present invention.

Referring to FIG. 10 there is shown a schematic diagram of another form of control unit according to the present invention.

The control unit includes a temperature probe comprising platinum wire 201. The platinum wire may be inserted into the core member of the cryo-cell assembly previously described in any suitable position.

A biasing current e.g. 2.5 mA may be applied to platinum wire 201 via resistor R10 and variable resistor VR1.

The voltage generated across platinum wire 201 is applied to the input of amplifier 202 (circuit type 308A). Offset of amplifier 202 is adjusted via variable resistor VR2. The output of amplifier 202 is scaled to represent actual temperature and is displayed on digital voltmeter 203 (circuit type DPM50).

The output of amplifier 202 is connected via signal limiting circuit 204 to a comparison circuit shown generally at 205. Signal limiting circuit 204 includes amplifier 206 and zener diode 207. Signal limiting circuit 204 is adapted to limit temperature control to −44° C.

Comparison circuit 205 includes a current summing junction 208 at the inverting input of amplifier 209. The summing junction receives positive current from amplifier 206 and negative current input from digital to analogue converter (DAC) 210. When the two currents are equal and opposite the output of amplifier 209 is zero. DAC 210 comprises a circuit type DAC 0800.

DAC 210 is fed with digital data stored in EPROM 211. EPROM 211 is adapted to store one or more temperature cycles or programs for freezing and/or thawing given biological materials. EPROM 211 comprises a device type MM 27C16.

EPROM 211 is driven by an address generator comprising counter 212. Counter 212 comprises a circuit type CD4040 12 stage binary counter providing an 8 bit address to EPROM 211. The eight address lines are also connected to means for displaying elapsed program time. The latter means comprises digital to analogue converter 213 and digital voltmeter 203. Digital voltmeter 203 includes a turn over switch 214 for selecting display of temperature or elapsed program time. Elapsed time, is preferably displayed as a percentage of total program time.

A 3-bit thumbwheel switch 214 is also connected to EPROM 211. Thumbwheel switch 214 may be used for selecting a given temperature program or cycle stored in EPROM 211.

Address generator counter 212 is fed with clock pulses along line 215. Clock pulses are provided by a clock generator including an oscillator shown generally at 216. Oscillator 216 comprises a feedback network including crystal element 217, capacitors C10 and C11 and resistors R11 and R12. The feedback network is connected around an inverter provided by integrated circuit element 218. Integrated circuit 218 comprises a 14-stage binary counter and is used as a frequency divider. Divider 218 may be set to divide by $2^{14}$. Divider 218 may comprise a device type CD 4060. The output of divider 218 is connected to a further divider 219. Divider 218 is connected to divider 219 via a run/hold switch 220. Switch 220 is provided for blocking clock pulses to divider 219. Switch 220 may be used to start a program sequence or to pause in the sequence at any time.

The output of divider 219 is connected to address generator counter 212 via a turn over switch 221. Turn over switch 221 is adapted to adjust the frequency of pulses supplied to counter 212.

The frequency may be selected between a fast run speed (1.7 Hz) or a relatively slow run speed (0.12 Hz). Switch 221 connects the selected frequency pulses to counter 212 via NAND gate 222. NAND gate 222 may be disabled via 8 input NAND gate 223. NAND gate 223 provides a disable pulse to NAND gate 222 when counter 212 reaches the end address of the program thereby stopping the program.

Reset switch 224 is provided for resetting counters 212, 218 and 219.

The output of amplifier 209 will swing high or low depending on whether the 'actual' temperature is higher or lower than the 'desired' temperature. The output of amplifier 209 drives a heater control circuit. The heater control circuit includes a pulse width modulator shown generally at 225 and a solid state switch including a darlington pair 226.

Pulse width modulator 225 includes comparator 227 and an integrating circuit comprising resistors R13, R14 and capacitors C12, C13. The integrating circuit receives substantially a square signal from counter 218 and converts these to a rising and falling ramp signal at the inverting input of comparator 227.

Comparator 227 compares the reference voltage at one of its inputs representing high/low temperature with the instantaneous ramp voltage at the other input. The output of comparator 103 is low when the reference voltage is higher than the ramp voltage and high when the reference voltage is lower than the instantaneous ramp voltage.

Comparator 227 is adapted to switch the darlington pair 226 into conduction when its output is high and hence supply power to heater 240.

An alarm circuit is shown generally at 228. Alarm circuit 228 is adapted to provide a visual or audible alarm of over or under temperature. Switch 229 may be used to select the visual or audible alarm. Alarm circuit 228 includes a pair of comparators 230, 231. The common output of comparators 230, 231 is high whenever the actual temperature is under or over the desired temperature.

Switch 229 selectively connects the output of comparators 230, 231 to a buzzer 232 or an LED diode 233.

A display is also included for indicating that the program is running. The latter includes comparator 234 and LED diode 235 connected to its output. The input of comparator 234 is driven by the output of NAND gate 222.

Amplifiers 202, 206 and 208 may each comprise a device type LM308. Comparators 227, 230, 231 and 234 may comprise a device type LM339, quad comparator.

The power supply for the control unit is conventional and is shown generally 236. The power supply includes regulators 237, 238, 239. Regulators 237, 239 may comprise device types LM7815 and LM7915 respectively and regulator 238 may comprise a device type LM7805. The power supply preferably is adapted to operate on 110/220/240 volts.

Figure 11:
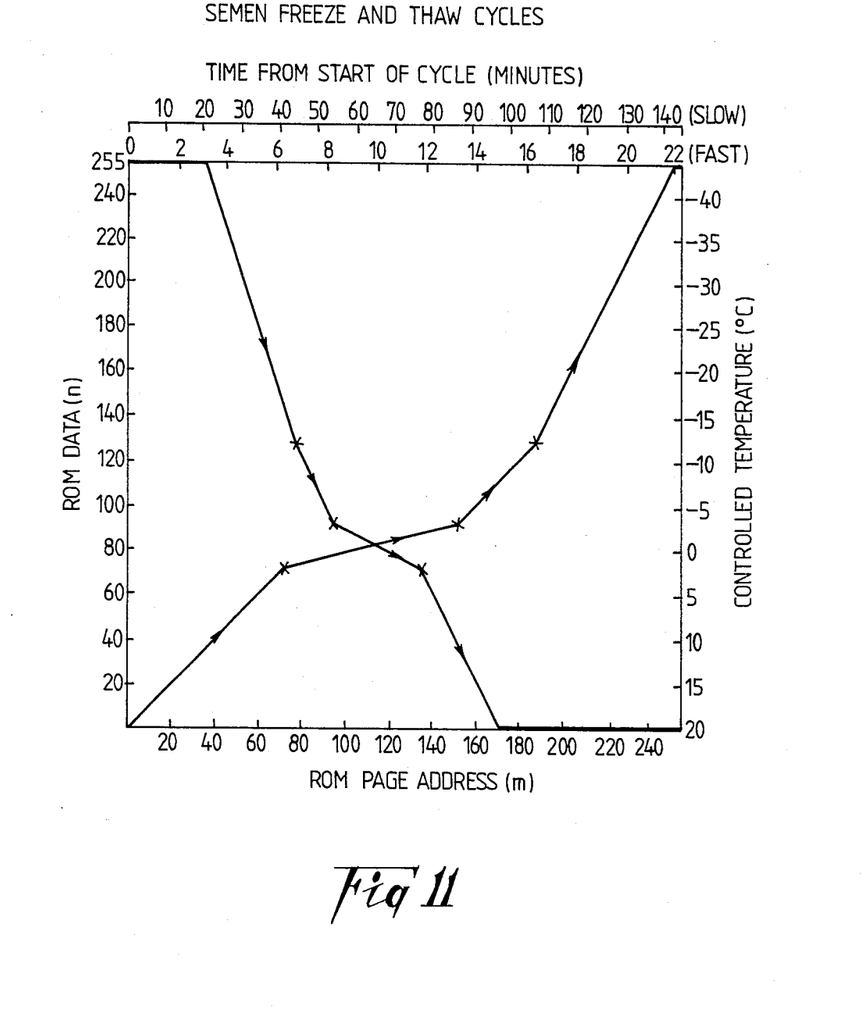
FIGS. 11 and 12 show preferred freeze/thaw temperature cycles for semen and embryo specimens respectively.
Figure 12:
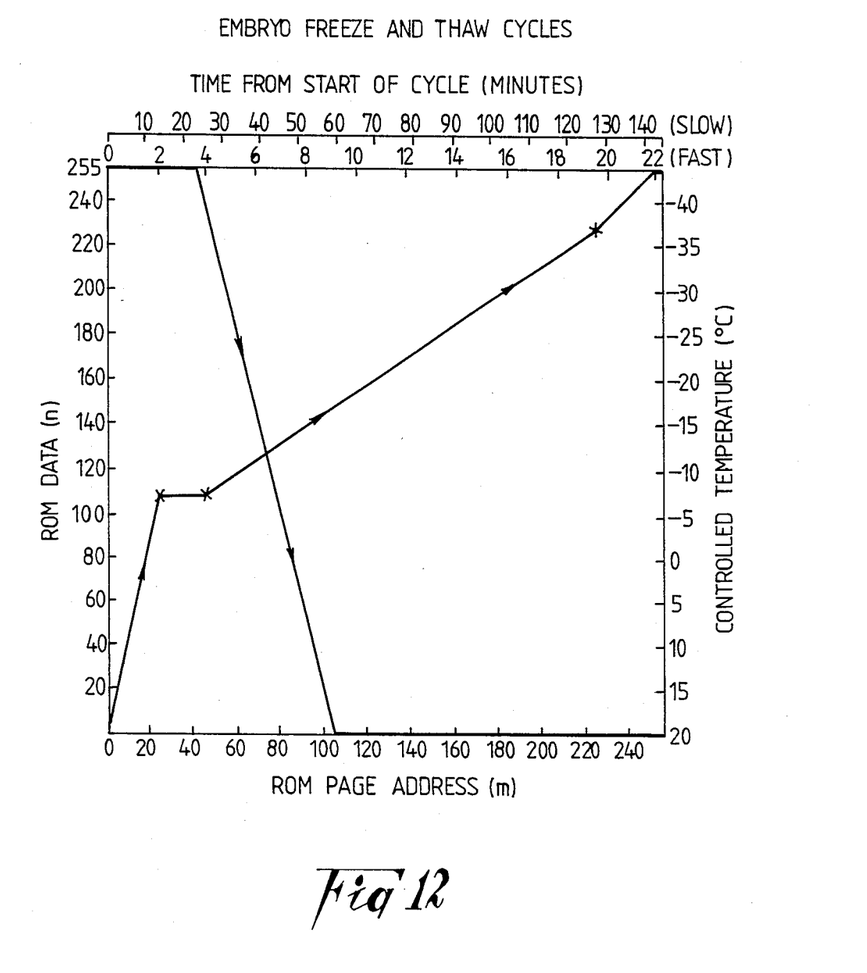

FIGS. 11–12 show typical temperature freeze/thaw cycles which may be programmed into EPROM 211.

The cryo-system of the present invention may be set up for freezing as follows:

Power is connected to the control unit and switched on.

A temperature cycle is selected on thumbwheel switch 214 and run/hold switch 220 is set to hold.

Switch 224 is reset and the appropriate program speed is selected on switch 221.

The cryo-cell assembly is placed in an insulated vessel and connected to the control unit. The insulated vessel is slowly filled with $LN_2$. After about 3 minutes the internal temperature gradients should stablize and the system is ready for freezing.

Specimen straws may now be inserted into the cryo-cell slots and the cell is covered with a lid. Switch 220 is set to run. The vessel should be inspected from time to time to ensure that sufficient coolant is present (not less than ¼ full).

When display 235 has stopped flashing the cycle is complete. Digital voltmeter 203 should then be displaying 100% elapsed program time confirming that the cycle is complete. The straws may be extracted and transferred to storage, although this is not urgent.

The procedure for thawing is similar but the cryo-cell assembly should be cooled before starting. This may be hastened by adding a little coolant to the inside of the cryo-cell.

The actual straw temperature may be monitored and/or recorded during a cycle with say a voltmeter and/or chart recorder connected to the control unit temperature display output.

The apparatus of the present invention may be adapted to precisely control freezing and thawing cycles of biological material using pre-programmed temperature functions.

The temperature cycles can be reprogrammed to suit particular types of materials and preparations. Different temperature cycles can be stored in the memory of the unit, and any of these can be selected for use. Temperatures can be increased or decreased at specified rates; or held for a specified period of time. Such variations can occur within any program. In one form the system of the present invention can control temperatures between +20° C. and −44° C. in steps of 0.25°.

Further advantages of the system include:

The cryo-cell and control unit of the present invention may be made highly portable and rugged for the field use. Power for the control unit may be supplied from a car battery. Consumption of coolant may be relatively low—less than 1 liter of liquid nitrogen per hour.

The system additionally is simple and convenient to use. Sample straws can be easily loaded into and extracted from the cryo-cell. The cryo cell can be readily cleaned. There are no moving parts to maintain—no mechanical pumps, or solenoid valves.

Operation may be performed by selecting the desired cycle, pressing the reset button, and switching the system to run. Temperature indication may be provided by an analogue output, calibrated e.g. as 1 volt per 10° C., over the range +40° to −200° C. A manual override may be available to stop at a particular temperature or to remove temperature control.

The control unit may provide information on cycle time and temperature matching. The design of the cryo-cell may be such that each individual straw experiences the same temperature cycle, and along each straw the temperature varies by no more than say 0.2°. Specimen straws may be held in a dry environment without contamination from buffer fluids, and no frost build up.

It will be appreciated that various alterations, modifications and/or additions may be introduced into the constructions and arrangements of parts previously described without departing from the spirit or ambit of the present invention.

Having now described our invention, what we claim as new and desire to secure by letters Patent is:

1. A cyro-cell assembly for freezing/thawing biological material, said assembly including a core member having a substantially circular cross-section, a plurality of spaces formed in said core member for receiving said biological material, said core member being adapted for conducting heat from said spaces to a cryogenic heat sink, said assembly including heat generating means in heat conducting relationship with said spaces and said spaces being arranged such that they intercept common isotherms which lie substantially along concentric cylindrical surfaces.

2. A cryo-cell assembly according to claim 1 including an under/over temperature alarm.

3. A cryo-cell assembly according to claim 1 including an outer member spaced from said core member and an insulating layer intermediate said core member and said outer member.

4. A cryo-cell assembly according to claim 3 wherein said core member and said outer member are tubular.

5. A cryo-cell assembly according to claim 4 wherein said spaces comprise slots formed longitudinally in said core member suitable for receiving straws bearing specimens of biological material.

6. A cryo-cell assembly according to claim 5 wherein said slots are formed around a perimeter of the tubular core member.

7. A cryo-cell assembly according to claim 1 wherein said core member comprises high purity aluminum.

8. A cryo-cell assembly according to claim 1 wherein said heat generating means comprises a heater element.

9. A cryo-cell assembly according to claim 1 wherein said heat generating means comprises a heater element wound around said core member.

10. A cryo-cell assembly according to claim 1 wherein said heat generating means includes a supply unit for supplying power to said heat generating means in accordance with a desired temperature cycle.

11. A cryo-cell assembly according to claim 10 wherein the supply of electrical power to said heat generating element is pulse-width modulated and the width of the pulses is controlled by the output of the comparator means.

12. A cryo-cell assembly for biological material according to claim 1 further comprising:
a supply unit for supplying electrical power to said heat generating means in accordance with a desired temperature cycle, said supply unit including actual temperature sensing means for sensing actual temperature associated with said spaces; memory means for storing the desired temperature cycle; comparator means for comparing the desired temperature and the actual temperature; and heat control means responsive to the comparator means for supplying electrical power to said heat generating element whenever the actual temperature falls below the desired temperature.

13. A cryo-cell assembly according to claim 12 wherein said means for sensing actual temperature is located in one of said spaces.

14. A cryo-cell assembly according to claim 12 wherein said memory means comprises a read only memory and said desired temperature cycle is stored in said memory in digital form.

15. A cyro-cell assembly according to claim 14 further including digital-to-analogue conversion means for converting the stored temperature cycle to analogue form prior to comparison with the actual temperature.

* * * * *